United States Patent [19]

Chamuel

[11] Patent Number: 4,523,473
[45] Date of Patent: Jun. 18, 1985

[54] MAGNETO-ELASTIC MATERIAL DEFECT DETECTOR

[75] Inventor: Jacques R. Chamuel, Framingham, Mass.

[73] Assignee: The Charles Stark Draper Laboratory, Inc., Cambridge, Mass.

[21] Appl. No.: 521,327

[22] Filed: Aug. 8, 1983

[51] Int. Cl.³ ............................................. G01N 29/04
[52] U.S. Cl. ......................................... 73/643; 73/583
[58] Field of Search ........................... 73/643, 583, 587

[56] References Cited

U.S. PATENT DOCUMENTS

| | | | |
|---|---|---|---|
| 4,348,903 | 9/1982 | Sato et al. | 73/643 |
| 4,395,913 | 8/1983 | Peterson | 73/643 |
| 4,434,663 | 3/1984 | Peterson et al. | 73/643 |

OTHER PUBLICATIONS

"Non-contact Ultrasonics", by Parkinson et al., Jul. 77.

*Primary Examiner*—Anthony V. Ciarlante
*Attorney, Agent, or Firm*—Weingarten, Schurgin Gagnebin & Hayes

[57] ABSTRACT

A dark-field magneto-elastic non-destructive testing technique for detection of defects in a conductive material by inducing eddy currents or applying an electric current to the material along a path in such manner that the current will be diverted from the path in the vicinity of any material defect, causing the generation of acoustic waves locally from the interaction of the diverted current with a local magnetic field. The resulting acoustic waves are detected as an indication of the presence and location of a material defect. In typical application, a current is induced in the conductive material by the generation of eddy currents in the material along a substantially linear path by coupling from a current excited wire insulated from and applied near the surface of the material. The eddy current will tend to follow substantially the direction opposite of the current excited wire. This current will be diverted from the path by any material surface defect, creating a normal component which interacts with a magnetic field component substantially parallel to the path, providing for the generation of an acoustic wave within the material which are detected by an acoustic sensor applied along an edge or face of the material. Typically the acoustic waves are generated as the relative electromagnetic fields of the applied current and the local magnetic fields are varied with respect to each other. By pulsing or varying the applied current or applied magnetic field, the time between the generation of the acoustic pulse, which is relatively instantaneous at any location in the material, and the reception of the acoustic pulse at the detector provides an indication of the distance from the defect to the detector. An array of detectors may be used to triangulate the defect. The elastic waves are generated only in the presence of a defect by the defect giving three dimensional location information about the defect location, as well as other characteristics, in contrast to conventional ultrasonic NDE techniques, where the defect is used as a scatterer of incident ultrasonic waves.

26 Claims, 7 Drawing Figures

MAGNETO-ELASTIC MATERIAL DEFECT DETECTOR

FIELD AND BACKGROUND OF THE INVENTION

Reliable and accurate techniques for the non-destructive detection of defects in structural members, particularly in highly stressed members such as aircraft wings and certain military structures, permits extended safe and failure free use of such structural members and improves the efficiency of maintenance programs. Accordingly techniques for such defect detection are of great importance.

Prior art techniques for contactless non-destructive testing of conductive materials have utilized locally applied pure eddy currents or eddy currents interacting with a magnet to generate ultrasonic waves throughout the material under investigation.

The ultrasonic waves then propagate through the entire material. Where they intercept a defect; acoustic wave scattering occurs. Detection of a defect is dependent upon detection of a scattered wave within a background of substantial acoustic energy. Such detection can be difficult. Also, the resolutions of the prior art techniques in identifying with high dimensional precision the location of a defect had been low while at the same time techniques permitting rapid checking of large areas have not been available.

BRIEF SUMMARY OF THE INVENTION

Great advantages are achieved in the invention by converting the defect into a sound source, and not just a simple scatterer of sound waves where the signal to noise ratio is low. The invention utilizes a dark-field avoiding acoustic energy in the object under study, instead using the defects as the sole acoustic source.

The present invention utilizes a technique capable of rapid scanning of a large surface area for non-destructive defect detection while at the same time permitting precise location of defect position, characteristics, and size with a higher signal to noise ratio.

In accordance with the teaching of the present invention a conductive material such as an aircraft wing to be non-destructively tested for the presence of surface or near surface defects has an electrical current applied along a typically linear path over an extended length of the material. In a preferred embodiment, this current is applied by inductive coupling from a long, current excited wire placed near but insulated from a surface of the structural material. Eddy current effects generate a current within the structural material substantially parallel and of opposite sense to the current in the conductive wire. This current will travel along the path in a substantially straight line through the structural member until it encounters a defect, at which point a component transverse to the direction of the path will be generated. A magnetic field is typically applied by a portable source such as a permanent or electro-magnet with the field direction oriented parallel to the direction of current flow along the path. In the regions of current diversion from the path, where small transverse currents are generated in the vicinity of the defect, the interaction between these transverse currents and the perpendicular magnetic field causes a stress force within the structural member. Where either the current or magnetic field are modulated this stress force will generate an acoustic wave, such as an elastic wave, within the material typically travelling in all directions from the location of the defect. An acoustic or elastic wave sensor is placed at some point on the structural member to sense such acoustic waves and provide an indication of their presence. The time elapsed between the generation of the acoustic wave resulting from the initiating pulse in the current or magnetic field and the time of reception of the acoustic wave gives an indication of the distance from the sensor to the defect. In the absence of a defect, no acoustic energy is produced by the parallel current and magnetic field. There is thus no background signal to impair detection of the acoustic signal originating at the defect and a high signal to noise ratio is possible.

Because of the finite size of the current inducing wire and the resulting narrow dimensions of the current path along the structural member, a high resolution is achieved in the identification of the defect location. Triangulation sensors may be utilized if desired for purposes of precise defect position identification. The current applying wire can be drawn across the surface of the structural member in order to scan a relatively large surface area. Where necessary the magnetic field is moved together with the wire or alone along the wire from one end to the other thereby accomplishing two dimensional surface area defect scanning.

DESCRIPTION OF THE DRAWING

These and other features of the present invention are more fully setforth below in the solely exemplary detailed description of the invention in the accompanying drawing of which.

DETAILED DESCRIPTION

The present invention contemplates the non-destructive detection of defects at or near the surface of a conductive material by applying a current along a path in the material and at the same time applying a substantially parallel magnetic field coextensive with the current path. In the absence of a defect, no acoustic signal is generated and there is thus little background noise. A surface defect or irregularity in the current path will cause the generation of a transverse component which will interact with the magnetic field to produce a local stress within the material in the vicinity of the defect. By pulsing or modulating the stress, a travelling acoustic wave is generated which can be sensed by one or more acoustic or elastic wave sensors applied to the structural member with the time of reception of the acoustic wave at each member providing an indication of the presence and location of the defect. Materials or structural members which may be non-destructively tested in accordance with the present invention include commonly stressed elements of which aircraft wings are one example.

Figure 1:
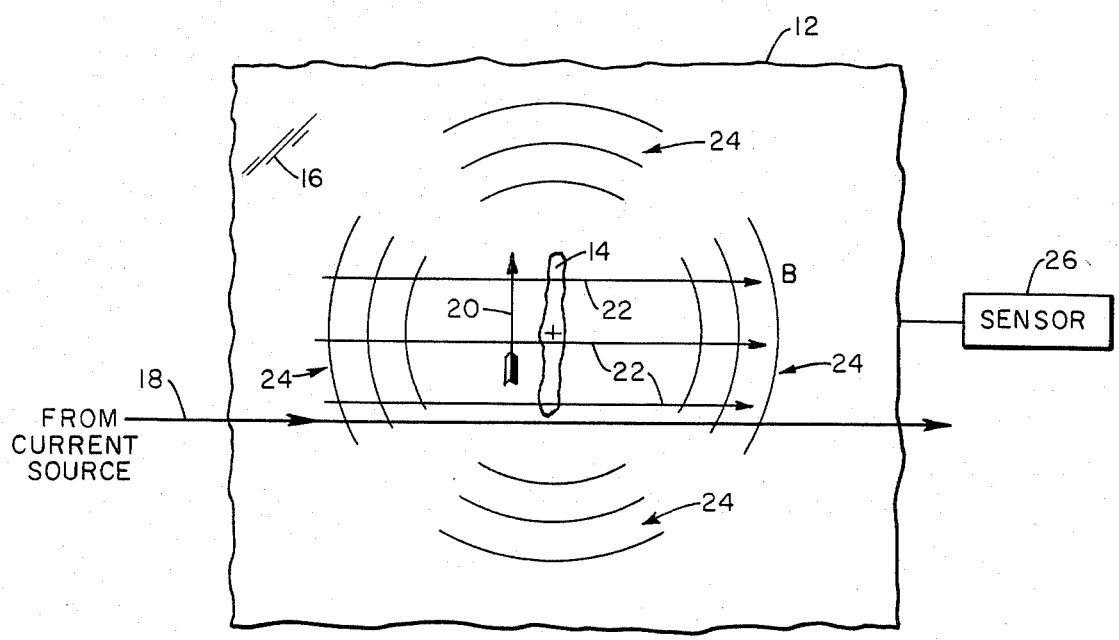
FIG. 1 is a diagrammatic view of the principles of the non-destructive defect detection according to the present invention.

FIG. 1 illustrates a section of a material 12 representing a structural member to be non-destructively tested for surface defects such as an irregularity 14 in the surface 16 of the element 12. For non-destructive testing to locate irregularity 14, a current, typically pulsed or varied in magnitude, is applied through the material 12, particularly along its surface over some linear distance or path 18. In the vicinity of the defect 14, the current will tend to deviate from the substantially straight line path 18 generating a transverse component 20. A magnetic field 22 is applied at the time of generation of the electric current along the path 18 in a direction substantially parallel to the path 18 and coextensive with it. The interaction of the magnetic field 22 and the transverse current component 20 creates a local pressure or stress within the material 12 only in the vicinity of the defect 14. When either the magnetic field 22 or current along the path 18 are varied or pulsed, this stress will generate a travelling acoustic or elastic wave 24, shown to travel outwardly from the location of the defect 14 in substantially all directions. An acoustic sensor 26, which may be any convenient form of sensor, is applied at a face of the material 12 to respond to the acoustic wave 24 and provide an output indication of its presence. Any combination of pulsed or A.C. burst current together with D.C. pulsed or low frequency varied magnetic field that varies the local stress force may be used to generate the acoustic wave travelling outward from the defect. The current or field may be code modulated and detected in a correlator to further enhance the signal-to-noise ratio.

Figure 2:
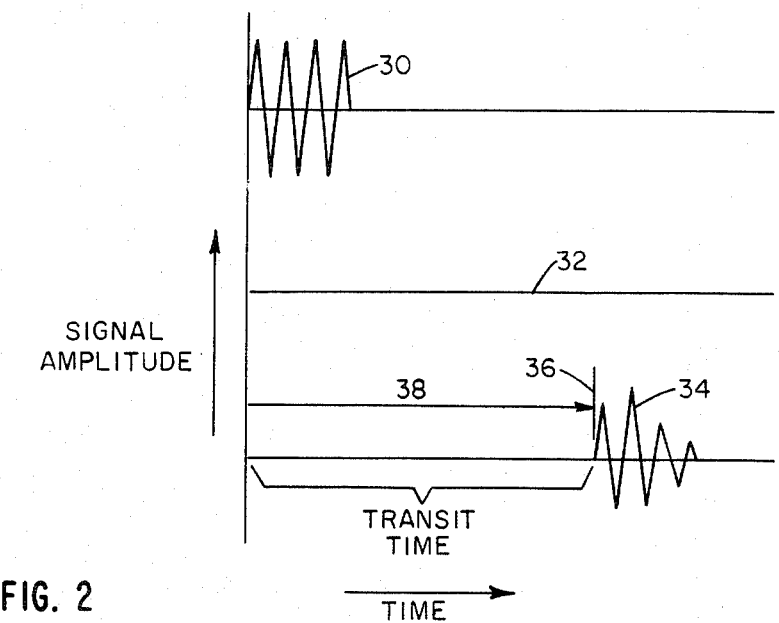
FIG. 2 is a representation of a typical output indication useful in identifying the presence and location of a defect.

FIG. 2 illustrates a typical waveform 30 corresponding to the A.C. current burst supplied along the path 18. A typical quiescent output signal from the sensor 26 (in the absence of a defect in the path 18) is illustrated by the waveform 32. Where a defect at or near the surface of the element 12 is located substantially within the path 18 for the current pulse an output waveform 34 is generated. As illustrated by waveform 34, an acoustic signal will substantially and suddenly appear at a point in time, illustrated by point 36, having a predetermined time delay after the initiation of the pulse or waveform 30. That predetermined time delay, represented by the vector 38, corresponds to the propagation time for the acoustic wave to travel from the location of the defect 14 to the sensor 26 over the shortest path. That propagation time, correlated to the speed of sound within the material 12, provides an indication of the distance of the defect 14 from the acoustic sensor 26. By controlling the location of the path 18 to a narrow dimensional region using techniques described below, and by placing the sensor 26 at a point along an extension of the path 18, the position of the defect along the path 18 can be precisely located to very high resolution. Because the path 18 is precisely defined in the vertical sense of FIG. 1, the exact location of the defect 14 can be very precisely located within fractions of a millimeter.

Figure 3A:
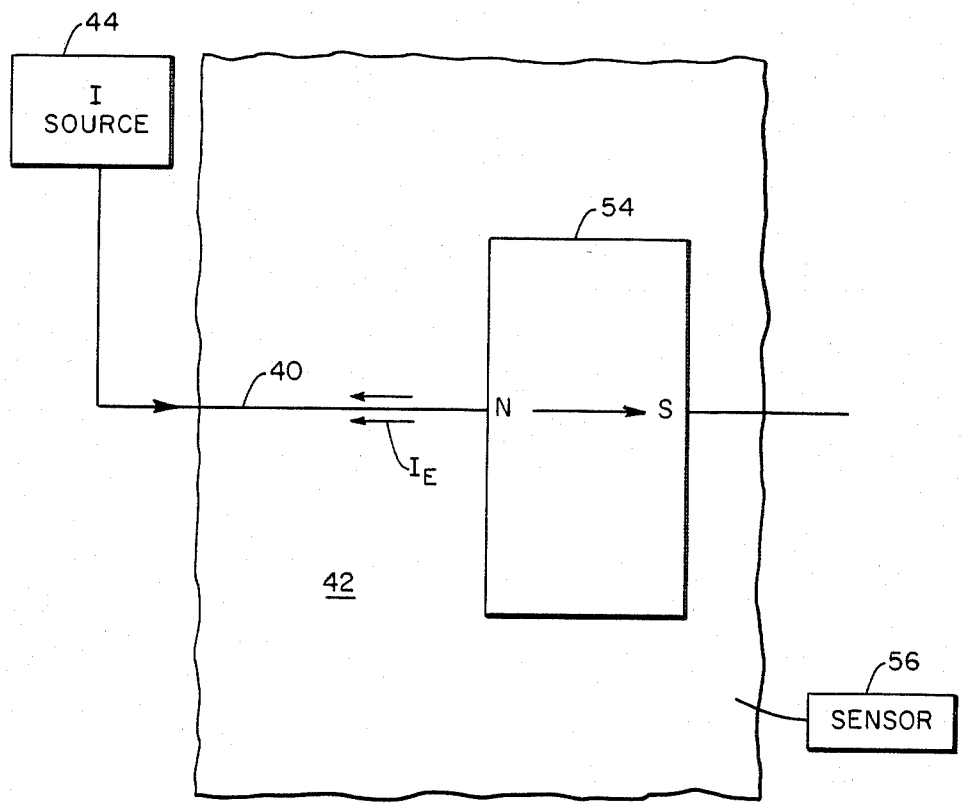
FIGS. 3A and 3B diagram apparatus for use in practicing the present invention.
Figure 3B:
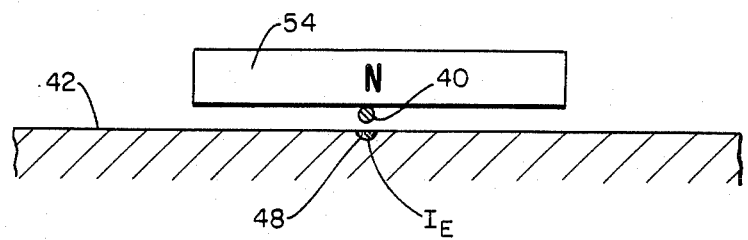

FIGS. 3A and 3B illustrate apparatus for exciting current through the conductive element under study using a long wire 40 placed proximate to but insulated from a surface 42 of the material under study. A current source 44 applies a burst or pulse of current to the wire 40 creating a magnetic induction field which passes through the surface 42 of the material under study, generating a current $I_E$ parallel to and in an opposite sense from the current in the conductor 40. Because the wire 40 can be made of a very thin dimension, and can be closely placed to the surface 42, the path 48 occupied by the induced eddy current, $I_E$ can be very narrowly defined. As the current on the path 48 passes a defect in the surface 42, transverse current components will be generated at the defect location.

A magnetic field is typically generated parallel to and coextensive with the path 48, by a portable or movable field source such as a magnet 54. The field 54 may extend along some or all of the path 48 distance. The wire 40 and the magnet 54 may therefore be placed in proximity to the path 48 as shown in the figure.

The interaction between the varying transverse current components and the magnetic field will generate an acoustic wave travelling throughout the element under study. An acoustic sensor 56 is typically placed at some location which may include attachment to a portion of the surface 42, typically to respond to the portion of the acoustic wave generated by a defect (not shown) where the acoustic wave travels substantially parallel to the path 48. Additional sensors may be utilized for purposes of triangulation if desired.

Because the location of the path 48 is precisely defined, a single linear dimension is established along which a defect may be known to exist, whenever the output indication from an acoustic sensor 56, such as illustrated by the wave form 34 in FIG. 2, is present. The precise location along the path 48 is then determined by the delay time interval, as represented by the vector 38 in FIG. 2, between the initiation of current along the path 48 and the reception of an elastic wave of significant amplitude by the sensor 56. The entire surface area may be scanned by moving the wire 40 and magnet 54 in a direction substantially orthogonal to the path 48 thus sweeping of a surface area of desired size.

Figure 4:
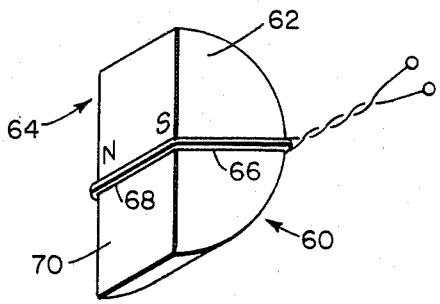
FIG. 4 shows one embodiment of a probe for applying, a parallel magnetic field and current.

A probe for applying a magnetic field and parallel electric current is illustrated in FIG. 4. As shown there, a permanent magnet 60 in the shape of a sectioned disc is magnetized to have the north and south poles on the opposite faces 62 and 64 of the disc. A coil 66 is wound with a segment 68 crossing the face 70, between faces 62 and 64, parallel to the lines of the magnetic field between faces 62 and 64. The probe of FIG. 4 is used by applying face 70 adjacent to the surface of the material to be investigated.

Figure 5:
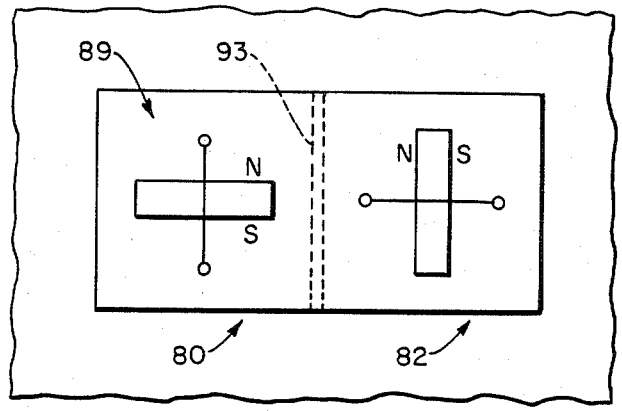
FIG. 5 illustrates a probe of orthogonal elements.

A probe as is illustrated in FIG. 5 may comprise two current and magnetic field source 80 and 82 set on a magnetic return path support 89 and separated by magnetic field decoupler 93 so that the parallel current and field sets of each probe 80 and 82 are orthogonal to each other. Because a single probe will be more sensitive to defects having a long dimension orthogonal to a parallel field and current set, the probe of FIG. 5 provides high sensitivity to any defect orientation.

Figure 6:
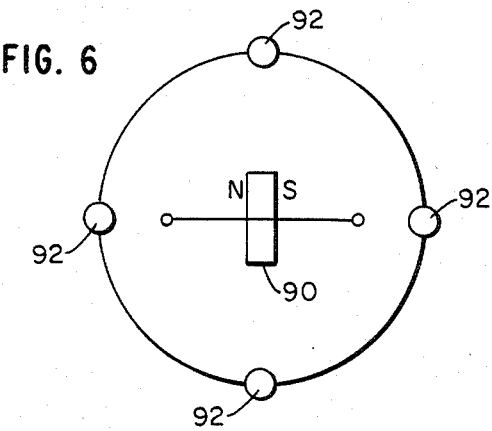
FIG. 6 shows a probe with an array of sensors.

FIG. 6 illustrates a probe having a central source 90 of parallel current and magnetic field according to the invention and including an array of acoustic sensors 92 integral with the probe. The source 90 and sensors are adapted to be placed adjacent to the surface under study such that the sensors are in acoustic wave receiving relation to that surface while the source 90 is adapted to induce a current therein parallel to a magnetic field.

Rapid and efficient defect detection and precise defect location are thus enabled in accordance with the teaching of the present invention. The actual scope of the invention is to be solely determined from the claims which follow.

What is claimed is:

1. Apparatus for dark-field electromagnetic-acoustic detection of defects in a conductive material, comprising:
   means for creating an electric current along a path in said material that diverts from said path in the vicinity of any defect present in said material along said path;
   means for generating an acoustic wave within said material only in response to said current that diverts from said path in the vicinity of a material defect in such a way that the acoustic wave originates exclusively in the vicinity of the material defect but not in regions of the material free from defects; and
   means for detecting the acoustic wave to provide an indication of the presence of said defect.

2. The apparatus of claim 1 wherein said means for creating current further includes means for inductively coupling electrical current to said material.

3. The apparatus of claim 2 wherein said coupling means includes a wire adapted to extend along a surface of said material and insulated therefrom.

4. The apparatus of claim 1 wherein said creating means includes means for applying a varying current along said path.

5. The apparatus of claim 4 wherein said varying current includes a pulsed current.

6. The apparatus of claim 1 wherein said means for generating an acoustic wave includes means for applying a magnetic field parallel to said path.

7. The apparatus of claim 6 wherein said magnetic field applying means is adapted to provide variation of said magnetic field.

8. The apparatus of claim 6 wherein said magnetic field applying means includes a movable magnetic field applying means whereby said magnetic field can be applied selectively to portions of said material.

9. The apparatus of claim 1 wherein said means for detecting includes an acoustic sensor placed along an edge of said material and operative to sense elastic waves within said material.

10. The apparatus of claim 1 wherein said detector means includes means for providing an indication of the distance between the location of said detector means and the location of the diversion of said current from said path in the vicinity of a defect as a function of the transit time of said acoustic wave within said material.

11. The apparatus of claim 1 wherein said acoustic wave is pulse coded and said detecting means include means for recognizing said code.

12. The apparatus of claim 6 including at least two orthogonally disposed ones of said current creating and magnetic field applying means.

13. The apparatus of claim 1 including:
   a probe having associated therewith for placement adjacent to said material said current creating means, said acoustic wave generating means, and at least one said detecting means.

14. Apparatus for dark-field non-invasive inspection of a conductive material having a region of defects and a region free of defects, comprising:
   means coupleable to said conductive material in both of said regions for producing an acoustic wave originating solely at the region of said defects in said material and not from said region free of defects; and
   means coupleable to said conductive material for detecting said acoustic wave originating solely in the region of said defects.

15. A method for dark-field electromagnetic-acoustic detection of defects in a conductive material comprising the steps of:
   creating a current along a path in said material that diverts from said path in the vicinity of any defect present in said material along said path;
   generating an acoustic wave within said material only in response to current that diverts from said path in the vicinity of a material defect but not in response to said current along said portion in regions along said path remote from the vicinity of any defect; and
   detecting the acoustic wave originating solely in the vicinity of a material defect to provide an indication of the presence of said defect.

16. The method of claim 15 wherein said current creating step further includes inductively coupling electrical current to said material.

17. The method of claim 15 wherein said creating step includes applying a varying current along said path.

18. The method of claim 17 wherein said varying current includes a pulsed current.

19. The method of claim 15 wherein said acoustic wave generating step includes applying a magnetic field parallel to said path.

20. Method of claim 19 wherein said magnetic field applying step is adapted to provide a variation of said magnetic field.

21. Dark-field apparatus for providing non-destructive and non-invasive testing for defects in a conductive structural member to be tested, comprising:
   means for applying an electrical signal along an intended path within the conductive structural member for propogation in a direction along the intended path;
   means for applying a magnetic signal having a field direction along the same path of the conductive structural member and in such a way that the field direction of the magnetic signal is always locally parallel to the direction of propogation of the electrical signal along the intended path;
   at least one of said electrical signal and said magnetic signal having a nonconstant magnitude; and
   means coupleable to said structural member for detecting acoustic energy present in the structural member and originating only in the region of the defects thereof as a result of the interaction of the applied electric and magnetic fields.

22. The invention of claim 21, wherein said intended path is a linear path.

23. The invention of claim 22, wherein said structural conductive member to be tested has end portions, and wherein said linear path extends substantially between said end portions.

24. The invention of claim 22, wherein said conductive structural member has end portions, and wherein said linear path extends between a portion of the structural member defined between said ends thereof.

25. The invention of claim 21, wherein said non-constant magnitude is pulsed.

26. The invention of claim 21, wherein said non-constant magnitude is analog.

* * * * *